United States Patent [19]

Lincoff

[11] 4,299,227

[45] Nov. 10, 1981

[54] OPHTHALMOLOGICAL APPLIANCE

[76] Inventor: Harvey A. Lincoff, The New York Hospital, 525 E. 68th St., New York, N.Y. 10021

[21] Appl. No.: 86,348

[22] Filed: Oct. 19, 1979

[51] Int. Cl.³ .......................................... A61M 29/02
[52] U.S. Cl. .................................... 128/344; 128/1 R
[58] Field of Search .................. 128/349, 349 B, 325, 128/344

[56] References Cited

U.S. PATENT DOCUMENTS

| | | | |
|---|---|---|---|
| 2,210,744 | 8/1940 | Winder | |
| 2,862,497 | 12/1958 | Pagano | 128/349 B |
| 3,034,510 | 5/1962 | Kittel | 128/349 B |
| 3,435,826 | 4/1969 | Fogarty | 128/349 B |
| 3,467,101 | 9/1969 | Fogarty et al. | 128/348 |
| 4,154,243 | 5/1979 | Patel et al. | 128/349 B |

Primary Examiner—Stephen C. Pellegrino
Attorney, Agent, or Firm—Bert J. Lewen; Charles A. Blank; Alfred H. Hemingway

[57] ABSTRACT

A method of correcting retinal detachments through a small conjunctival incision wherein an expandable member is inserted into Tenon's space, the member is expanded, to form an indentation in the eye, and left in place until the subretinal fluid has absorbed and the retina has reattached.

3 Claims, 8 Drawing Figures

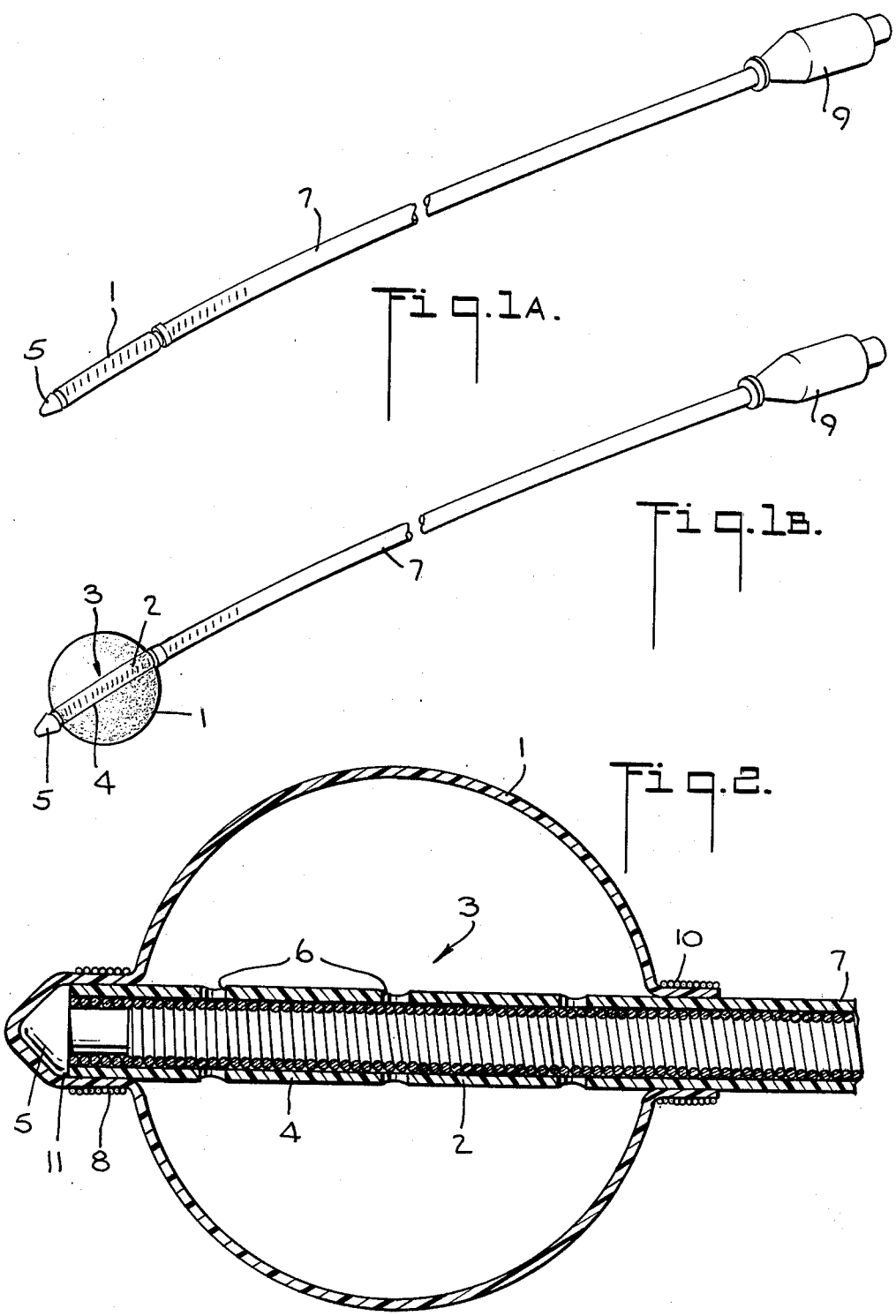

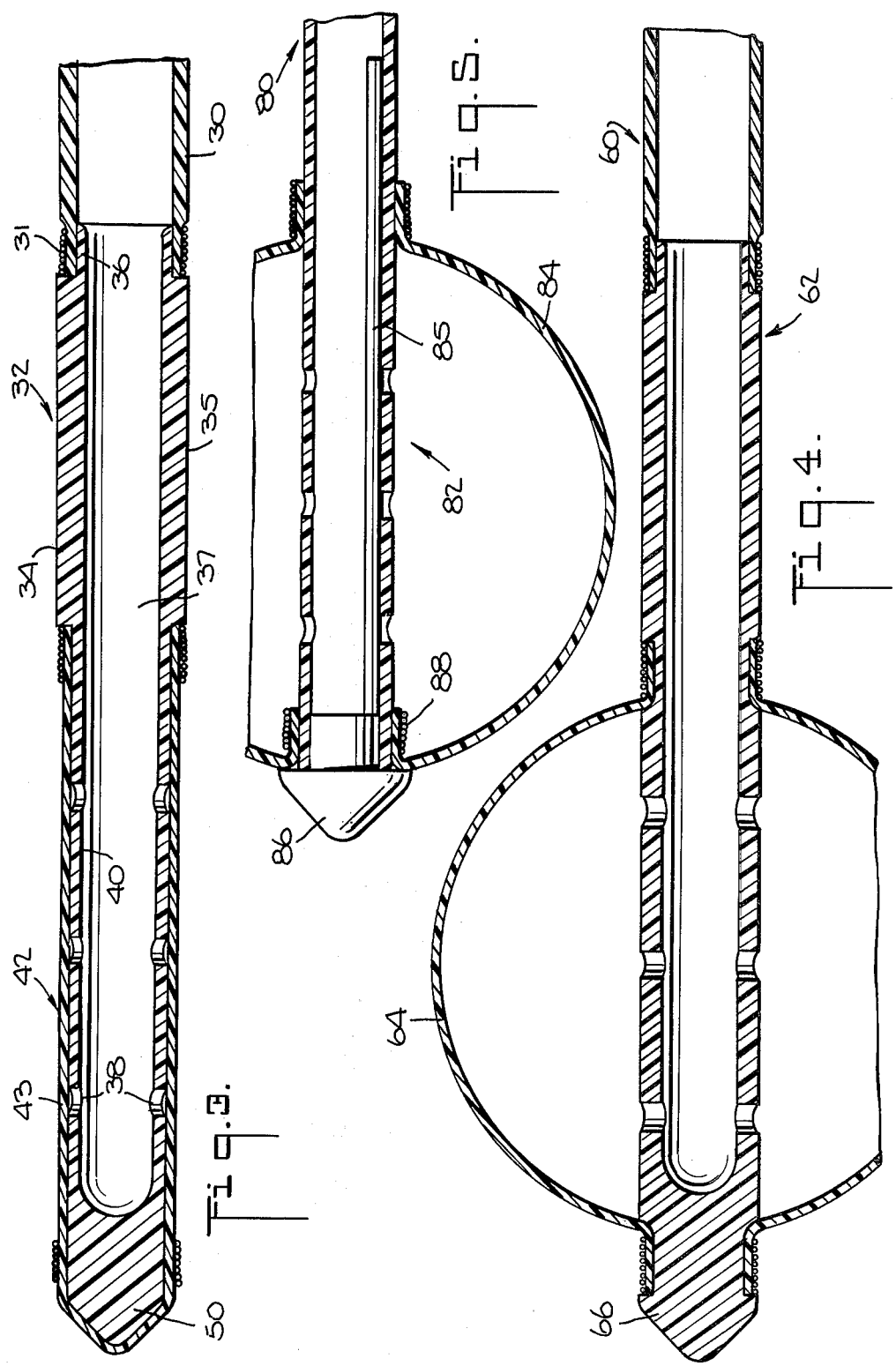

OPHTHALMOLOGICAL APPLIANCE

This invention relates to a novel appliance having a selectively expandable and collapsible portion and useful in various ophthalmological diagnostic and corrective procedures relating to retinal separation.

A means of maintaining scleral depression beneath a peripheral retinal break in a detached retina has been sought for some time. It has been thought that if such an indentation could be sustained for even a few hours subretinal fluid might be absorbed and the eye returned to the state that existed immediately after the tear occurred, when reattachment may have been effected by coagulation alone.

A number of extraconjunctival devices intended to permit the above-described procedure have been devised within the last few years, including a plastic adaptation of the Rosengren ring (see Rosengren, *Indentation of Sclera by Means of Silver Ball*, Mod. Probl. Ophthalmol. 3:144–148 (1965)), large sponges glued into the cul-de-sac and an extraconjunctival suction device used to hold a sponge in place.

Expandable devices per se have been used before in ophthalmological procedures, such as in the treatment of retinal detachment. Schepens et al. have used an intraocular balloon for manipulating giant tears. See Schepens and Freeman, *Current Management of Giant Retinal Breaks*, Trans. Am. Acad. Ophthalmol. Otolaryngol. 71:474–487 (1967); and Freeman, Couvillion and Schepens, *Vitreous Surgery: IV. Intraocular Balloon: Clinical Application*, Arch. Ophthalmol. 83:715–721 (1970). Banuelos et al. developed an expandable implant to be inserted beneath scleral flaps. See Banuelos, Refojo and Schepens, *Expandable Silicone Implants for Scleral Buckling: I. Introduction of a New Concept*, Arch. Ophthalmol. 89:500–502 (1973); Refojo and Banuelos, *Expandable Silicone Implants for Scleral Buckling: II. Experiments In Vitro*, Arch. Ophthalmol. 90:127–130 (1973); and Huamonte, Refojo and Banuelos, *Expandable Silicone Implants for Scleral Buckling: III. Experiment in Vivo*, Arch. Ophthalmol. 93:354–356 (1975). Hoepping sutured a balloon to sclera to buckle large posterior breaks and drained subretinal fluid to obtain retinal attachment. See Hoepping, *Die Ballonplombe*, Mod. Probl. Ophthalmol. 5:289–291 (1967).

Fogarty et al., in U.S. Pat. No. 3,467,101, describe a balloon catheter for probing lumenal portions of the body, the catheter having a soft rubber plug at the tip, a latex or plastic elastomer balloon portion set back from the plug, a valve and a tube with a hollow coiled wire core intermediate the valve and rubber plug. Fogarty, in U.S. Pat. No. 3,435,826, discloses an embolectomy cathether having a tip covered with soft pliable material, a rubber balloon, a valve and a flexible plastic tube intermediate the soft pliable tip and the valve. A biliary balloon probe sold by Edwards Laboratories under the mark Fogarty is of the general form described in the above Fogarty patents and has a natural rubber balloon and an extremely pliable tip, which may be stiffened by use of a stylet.

Prior to procedures made possible by the appliance of this invention, accomplishing the scleral buckling necessary to the reattachment of detached retinas required relatively major scleral surgery. Surgical approaches now employed to effect scleral buckling typically require a 180° incision and reflection of associated conjunctiva, Tenon's fascia and sometimes ocular muscles. The need for this extensive amount of surgery arises from the necessity of having to attach the device used to buckle the sclera by means of scleral sutures, scleral flaps, encircling bands or analogous measures. Associated with these surgical procedures is an approximate morbidity of about six percent in the form of hemorrhage, uveitis, infection and the like.

Procedures utilizing the appliance herein described do not require draining subretinal fluid and do not require securing the device used to accomplish scleral buckling. The temporary unsecured buckle provided by this invention permits reattachment of detached retina by way of a small conjunctival incision on the order of 2 mm in length, which corresponds to about 10° of the ocular circumference.

As used in the description of the invention herein, the word expandable denotes two aspects of the invention. One aspect is that prior to and during insertion of the new appliance into the eye the device is in a collapsed state, thereby presenting a relatively small cross-section perpendicular to the direction of travel in the eye; upon locating the expandable portion of the device in a desired position within the eye, the device may be inflated or otherwise expanded to attain significantly greater dimensions than those initially presented. A second aspect of the term arises from the fact that the eye typically has an internal pressure of about 20 mm Hg over atmospheric pressure. The closure of retinal breaks leading to detachment often requires a degree of scleral indentation which, if attempted in one fell swoop, would require drainage of subretinal fluid to preclude raising the internal pressure of the eye to an unacceptably high level. The drainage procedure has wellknown attendant risks. Therefore, it is most desirable to accomplish the total required indentation over a significant period of time rather than virtually instantaneously, and indeed this constitutes one aspect of the invention. When buckling is accomplished relatively slowly, the intraocular drainage mechanism can compensate and undesirably high pressures within the eye are avoided. Thus as the term expandable is used herein, it is necessary but not sufficient that a device according to the invention have an initial collapsed configuration and a final desired expanded configuration. It is also necessary that the device have the ability to assume configurations intermediate the initial and final ones, to permit gradual indentation of the eye to the final desired shape for closing the retinal break. Preferably the desired changes in shape of the expandable portion of the device over time will be continuous in nature rather than step-wise.

One object of this invention is to provide a temporary unsecured buckle useful in the treatment of retinal detachments and a method of using same. Another object of this invention is an inflatable appliance provided with a tip suitable for dissecting tissue. Still another object of the invention is an appliance having an expandable portion that may be in contact with bodily tissues and fluids for relatively long periods without adverse effect. A further object of the invention is an ophthalmological appliance comprising a dissecting tip, an expandable member and a substantially rigid tubular core within the expandable member. A still further object is an expandable appliance useful in a variety of ophthalmological procedures. Another object is to provide a method of reattaching detached retina that does not require draining subretinal fluid or a significant amount of surgery on the eye.

In contradistinction to the Fogarty devices, the instant appliance is not primarily an apparatus for probing lumenal body passages. Rather than being designed to travel along lumenary body passages without causing injury to associated tissue, the balloon and tip portion of the device here disclosed must be relatively rigid and capable of dissecting bodily tissues and be of at least sufficient stiffness to follow the route of a blunt probe through Tenon's space.

The ophthalmological appliance of this invention comprises a device having a dissecting tip adjacent an expandable and collapsible wall with an exterior surface that is non-reactive to bodily tissues and fluids for relatively long periods of time, i.e., from one to four weeks or so. For example, an elastic member consisting of an expandable wall or balloon portion surrounds a substantially rigid, nonexpandable tubular core and there are means permitting the passage of fluid in either selective direction between the interior of the tubular core and the interior of the elastic member. Such means will typically include at least one fluid passageway in communication with both the interior of the tubular core and the interior of the expandable member. A second tube, preferably soft, flexible and non-resilient and presenting an exterior surface that is non-reactive to bodily tissues and fluids for relatively long periods, has one end communicating with the tubular core and the other end with means for selectively permitting fluid to be (1) introduced into the expandable portion via the tube, (2) removed therefrom via the tube or (3) retained therein. In the most basic exemplification of the invention, the means may consist of a selfsealing rubber dam. A coil of steel wire or other suitable material may be included within an otherwise pliable tubular core of the balloon to provide sufficient stiffness or rigidity thereto and facilitate its passage through Tenon's space. Optionally, the tubular core may comprise a substantially rigid wire or plastic tube.

In the preferred form of the invention, the expandable member is a balloon and the preferred use is in the reattachment of retinal detachments caused by a single retinal break. In this procedure, the retinal break is localized with transconjunctival depression and the position of the break is marked on the conjunctiva with ink. The appliance tip, with balloon deflated, is inserted into the parabulbar space through a small incision in conjunctiva and then maneuvered to the area of the retinal break and expanded beneath it. Initially the balloon portion maintains its position by fixation between the eye and the bony orbit. As the eye decompresses, a depression in the globe is created in which the balloon is maintained by the epibulbar tissues. Little tendency for the balloon to move from this position is found after ocular rotations have been restored. The indentation in the globe acts like a scleral buckle: the retinal break closes, subretinal fluid absorbs and the retina reattaches.

The application of this invention also extends to diagnostic procedures, such as to confirm the presence of a possible break, to indicate the position of a secondary break, and to define pre-retinal traction. The insertion of the new appliance inflicts relatively little trauma and, when indicated, an operation by a standard procedure can follow without delay.

The unsecured balloon buckle described herein, in addition to being of value in the reattachment of retinal detachments caused by a single break and in the diagnostic processes previously described, is also useful in averting diplopia when the break is beneath a rectus muscle, buckling over thin sclera, and as a minimum procedure for surgical-risk patients.

FIGS. 1A and 1B illustrate one embodiment of a device according to the invention in the deflated and inflated modes, respectively;

FIG. 2 shows in detailed cross-section the dissecting tip, tubular core and balloon portions of the FIGS. 1A and 1B embodiment.

FIG. 3 illustrates in cross-section an embodiment of the invention having a sock-like balloon component covering the dissecting tip and a rigid tubular core;

FIG. 4 is a cross-sectional view of an embodiment having a tubular elastic material component and a unitary tip and tubular core;

Figure 6A:
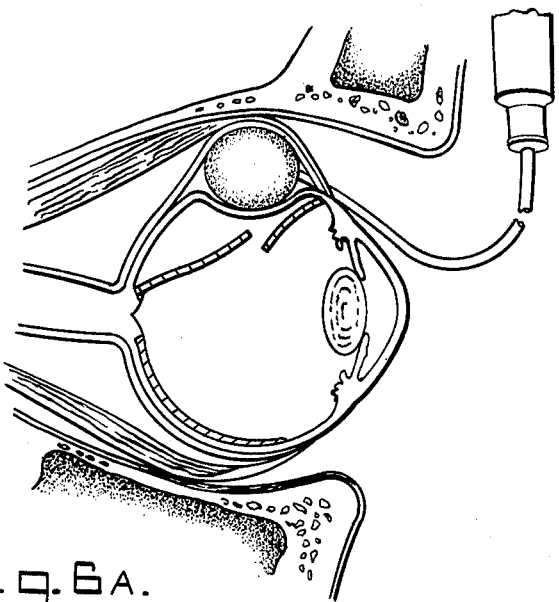
Figure 6B:
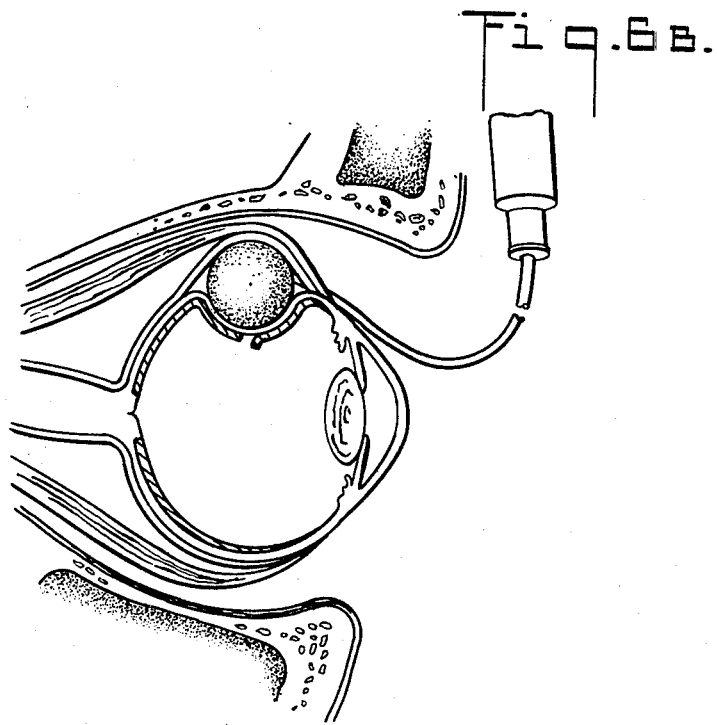

FIG. 5 is a cross-sectional view of an embodiment having a tubular balloon part, a tubular core stiffened by an axially positioned solid member adhered to the inner wall of the core, and a dissecting tip having relatively little extension beyond the inflatable balloon portion; and FIGS. 6A and 6B illustrate the conformation of the expanded balloon portion of the appliance of this invention and the eye (1) shortly after introducton to the eye and (2) after absorption of subretinal fluid and reattachment of the retina, respectively.

One embodiment of an appliance according to the invention is shown in FIGS. 1A and 1B, the former illustration depicting the expandable portion of the device in a relaxed mode and the latter figure showing the expanded configuration. As used herein, expandable also includes the connotation that the expanding element will return to its unexpanded configuration upon removal of the force(s) causing expansion. An expandable elastic envelope 1 surrounding the outer circumference of a rigid tubular core 3 is positioned intermediate a dissecting tip 5 and a tube 7 made of a flexible material. The tube 7, at the end opposite the end communicating with the expandable envelope or balloon 1, is provided with an adapter 9 that fits a standard syringe and comprises a valve that retains fluid. As shown, the outer diameter of the expandable portion of the deflated device is not substantially different in size than the maximum diameter of the tip 5 or the outer diameter of tube 7. The rigid tubular core 3 comprises a coiled spring 2 that extends the entire length of the balloon and also through a portion of tube 7 immediately adjacent the balloon, thereby imparting rigidity to what would otherwise be quite flexible portions of the device. FIG. 2 shows a large sectional view of the balloon and adjacent portions of the device illustrated in FIGS. 1A and 1B. Surrounding the coiled spring 2 inside the balloon 1 is an extension 4 of the tube 7 provided with a plurality of holes 6. Thus inflating fluid introduced through adapter 9 proceeds via tube 7 to the interior of coiled spring 2, through the fluid permeable interstices between adjacent coils of the spring where the holes in extension 4 are located, and into balloon 1. The coil, either of metal or a suitable synthetic material, extends through the entire inflatable length of elastic member 1 and up to a shoulder 11 on tip 5 at one end and part way up tube 7 on the other end. The winding forming the coil is not fluid tight and the interstices of same therefore, as indicated above, provide a plurality of fluid passageways in communication with the internal chamber of extention 4 and coil 2 and the interior of elastic member 1 by way of holes 6 in the wall of extension 4. Elastic member 1 comprises a tube open at one end and the closed end thereof surrounds the dissecting end of dissecting tip 5.

A fluid-tight joint between the closed end of the elastic member and one end of extension 4 is formed via adhesive (not shown) or winding 8, a combination thereof or any other suitable means. A similar joint is effected between the open end of elastic member 1 and the other end of extension 4. The non-dissecting end of tip 5 may be force fit into core 2 and secured by any suitable means, including adhesive and/or the aid of circumferential grooves (not shown) for the pertinent part of the winding forming coil 2. The tip 5 is sufficiently firm or rigid and suitably shaped so as to permit dissection of tissue, most notably that found in Tenon's space.

Depending upon the precise manner of use and desired functions, the expandable material forming the envelope 1 may be selected to provide various options. For example, the expandable material may comprise an elastic member fashioned of silicone rubber, which, although more fragile than other possible materials such as latex or natural rubber, permits some diffusion of inflating fluid into surrounding tissue, thus suggesting the possibility of including a beneficial component, for example an antibiotic to ward off infection, in the inflating fluid when a silicone rubber balloon is used. Silicone balloons have also appeared to be substantially non-reactive with bodily tissues in the procedures described herein. Latex, on the other hand, is tougher and less permeable than silicone rubber but evidence of some reaction with the eye has been noted where the device has been utilized as a temporary buckle in the treatment of retinal detachments and left in the eye for up to a week or so. Where diffusion is not desired and increased toughness and resistance to reaction with the eye are preferred, siliconized latex may be considered. The degree of stiffness or rigidity imparted to the balloon component and adjacent tube portion by the coiled tubular core of this embodiment may be varied. For example, the coil may be fashioned to provide sufficient stiffness to permit that part of the appliance to proceed in a straight path through Tenon's space but sufficiently flexible to reduce or eliminate the ability of the tip to penetrate Tenon's capsule. The tube 7 of this embodiment is quite soft and pliable in that portion not occupied by a part of the rigid tubular core and silicone rubber is the material of choice for this component. The fluid used to expand or inflate the balloon portion of the device may be varied as previously noted. Preferred fluids include sterile liquids not harmful to the human body in the event of leakage or balloon breakage, with liquids isotonic with body fluids, such as saline, usually being used.

Another embodiment of the invention appears in FIG. 3 in deflated form. Tube 30 leads from an adapter of the sort previously described (not shown) to a rigid tubular core 32. A sock-like or closed tube member 42 of suitable elastic material is snugly fitted over end portion 50 and adjacent portion 40 of core 32. The rigid tubular core may be of any substantially rigid material that is not detrimentally reactive with bodily tissues and fluids. It may, for example, be metal or plastic and machined, cast or molded. Rigid tubular core 32 as depicted comprises an outer diameter portion 34, of substantially the same outer diameter as undeformed tube 30 and unexpanded balloon portion 43, and reduced outer diameter portions 36 and 40. Reduced diameter portion 36 is contained within tube 30, which is joined to component 32 in any suitable fashion such as with adhesives (not shown) and/or circumferential windings 31. Reduced diameter portion 36 may also be provided with circumferential grooves (not shown) on its outer diameter to facilitate the joining or augment the strength of the formed joint. In similar fashion the inflatable portion 42 is joined and sealed at its open and closed ends to reduced diameter portion 40 of core 32. Rigid tubular core 32 as shown includes a central chamber 37 in communication with tube 30 and a plurality of holes 38 to establish fluid passages between chamber 37 and the interior of expandable member 42. To insure substantial uniformity of outer dimension and full return to the depicted configuration upon deflation, elastic member 42 is subjected to tension in a longitudinal direction prior to and during its joining to core 32. End portion 50, covered with elastic member 42, forms a dissecting tip integral with core 32 and is shaped to facilitate dissection of tissue through Tenon's space.

FIG. 4 is a cross-sectional view of an embodiment comprising tube 60, a rigid tubular core 62 and an inflatable member 64 and is similar to the device of FIG. 3 except that the expandable member is shown in an inflated mode and is formed as an open tube rather than as an elastic tube closed at one end and dissecting tip 66 is therefore not covered by the elastic member.

FIG. 5 illustrates an embodiment comprising tube 80, tubular rigid core 82, elastic member 84 and dissecting tip 86 and is similar to the variation of FIG. 2 except that the elastic member is open at both ends prior to assembly (and does not cover the dissecting tip), the distance between tip 86 and the closest expandable portion of member 84 is reduced by positioning the joint between member 84 and core 82 that is closest to tip 86 within the interior of member 84, rather than on the exterior, and rigidity is imparted to tubular core 82 by a longitudinally positioned member 85 rather than a coil. Stiffening member 85 may be formed of virtually any material compatible with the inflating fluid that will lend the desired degree of rigidity to the tubular core. As illustrated, member 85 is a round wire axially located and adhered to the inside wall of the tubular core. Assembly of this embodiment would require partially pulling the open tube comprising member 84 over tip 86, effecting joint 88, and then reflecting the remainder of member 84 over rigid tubular core 82 so that the surfaces are inside out with respect to their orientation when joint 88 is formed. Although as shown in FIGS. 5 and 2 the extension of tube 7 extending the length of the elastic member is shown to be continuous but for the holes in the tube wall communicating with the interior of the expandable member, the extension may be discontinuous, thereby increasing the degree of fluid communication between the interior of the tubular core and the elastic member.

The dissecting tip of a device according to the invention could be included within the expandable portion of the appliance. For example, a device of the general types shown in FIGS. 1A, 1B, 2 and 3, having an expandable portion comprising an elastic tube with one closed end, could be made without forming the balloon joint nearest the tip, thereby permitting virtually the entire elastic member to expand. Alternatively, in lieu of the aforementioned balloon joint the elastic member might be spot-welded or otherwise attached to the leading edge of the dissecting tip.

In the reattachment of retinal detachments by use of this invention, the eye to be treated is anaesthetized with a retrobulbar injection of 2 cc of 2% lidocaine or topical application of proparacaine hydrochloride. Retinal breaks are then localized transconjunctivally by depression and treated with the cryosurgical probe under ophthalmoscopic control. The procedure is the same as that used for phophylactic cryopexy except that the position of the break is marked on the conjunctiva with ink and its distance from the cornea is measured. The radian of the break is also marked anteriorly on the conjunctiva at the ora serrata. If the break is beyond the limits of the conjunctival cul-de-sac, only the radian of the break is marked and the anterior-posterior distance is estimated. Coagulation of posterior breaks by laser coagulation is achieved after the subretinal fluid has absorbed.

With localization complete, a 2 mm conjunctival incision is made through the mark at the ora and the deflated balloon is introduced into Tenon's space to the approximate depth of the break. The position of the balloon is ascertained ophthalmoscopically after partially inflating it with saline. Minor adjustments to bring the balloon immediately beneath the break are made if necessary by pushing the tube or slightly inflated balloon transconjunctivally with a wet swab.

Once in position, the balloon is expanded under ophthalmoscopic control to a size appropriate to the height of the detachment and the size of the break. Typically the total volume of the expanded portion at full desired inflation is between 0.75 and 1.25 cc. As the balloon expands, it raises intraocular pressure, making it necessary to monitor the central artery and to deflate somewhat if the artery threatens to close. The operation is completed by tying a preplaced suture at the site of the conjunctival incision. The suture stabilizes the exit of the silicone tube and secures the conjunctival edges around the tube in "purse string" fashion. Augmented stabilization of the tube at the entrance site may be obtained by taking a bite of episclera with the suture that "purse strings" conjunctiva around the tube. When the entrance is adjacent to a muscle insertion, a bite of tendon also serves to provide augmented stabilization of the tube. The tube and the valve at its end are taped to the forehead. The lids close easily over the tube. Both eyes are covered with dressings, and binocular patching is maintained until the subretinal fluid has absorbed, usually by the next day. FIG. 6A illustrates the relative configurations of the expandable portion of an appliance according to the invention and the eye shortly after the device is introduced to the eye and FIG. 6B shows the configurations after substantially all subretinal fluid has been absorbed. The transition of the expandable member from its initially expanded but compressed configuration between the eye and the bony orbit, here a balloon of initially ellipsoidal shape, to its finally expanded configuration, as illustrated in FIG. 6B a sphere, typically takes about three hours and, therefore, unsatisfactorily high pressures within the eye are avoided. The scleral buckling leading to full closure of the retinal break occurs gradually and virtually continuously over the period of time necessary to effect closure, with subretinal fluid being steadily absorbed thereafter. Photocoagulation with the argon laser is added around the breaks in eyes deficient in cryopexy. The long-term attachment will depend on the thermally-induced adhesion.

Although the original intent was to remove the appliance immediately after the reattachment of the retina, patients tolerate the device in place with so little discomfort that it is advantageous to leave it longer and thereby secure better adhesion. It is therefore recommended to reduce the volume of the expanded portion by withdrawing one-third of its contents on the fifth day and the remainder by thirds on the following two days. After the balloon is deflated, the suture at the insertion site is cut and the balloon is withdrawn under topical anaesthesia.

As prophylaxis against infection, a culture of the entry site may be made when the balloon is inserted and the patient treated topically with the appropriate antibiotic. In any event, ointment neosporin is usually applied when the dressing is changed each day. If reoperation is intended, the balloon and the suture at the entry site are removed at least 24 hours before. As previously noted, introducing antibiotic into the balloon for diffusion into the tissues is possible provided that the material used for the balloon is sufficiently permeable, as is silicone rubber.

Insertion of a blunt probe to the point of the break prior to introducing the new appliance into the eye may serve to both prepare a route for the tip and balloon through the parabulbar space and to confirm or correct the conjunctival localization. The latter consideration arises because transconjunctival localization may have a lateral error of as much as 3 mm if the eye has been rotated during localization.

The instant appliance, as earlier noted, is useful in diagnostic as well as corrective procedures, particularly in the investigation of problem detachments. For example, given a detachment in which a break cannot be found, the balloon may be used to test whether the area contains a retinal break by inflating it beneath an area of suspicion appropriately determined by the shape of the detachment. Prompt reattachment confirms the presence of a break. If partial reattachment occurs, the contour of the residual detachment points to the position of a second break. Inflating the balloon beneath a retinal break upon which there is apparent traction serves to define the degree of traction and the type of repair required.

The invention also has utility in corrective procedures other than the method previously described in detail. The temporary balloon buckle has eliminated diplopia as a sequel of scleral buckling when the retinal break is beneath a rectus muscle, especially a vertical rectus. This is more critical when the macula is attached preoperatively and full macular function can be expected. In such patients the conjunctival incision for the entrance of the balloon is made adjacent to the insertion of the tendon and the balloon directed obliquely beneath the muscle to the position of the retinal break. Within hours after the balloon is deflated and withdrawn, the muscle again functions normally. The temporary balloon buckle may be substituted for traditional forms of buckling when the sclera, as perceived through the conjunctiva, can be recognized as thin in the area of the break. The elimination of scleral sutures avoids the risk of inadvertent perforation as well as the possibility of scleral erosion that might occur beneath a more permanent scleral explant.

Use of the disclosed appliance dispenses with the need for scleral surgery for the treatment of uncomplicated detachments and provides a local buckle sufficient to close a modest retinal break. With the break closed, subretinal fluid absorbs and the eye returns to a state apparently similar to that which existed at the moment after the retinal tear occurred, when it might have been treated with coagulation alone. Use of the invention as an exploratory tool also serves to reduce the extent of surgery in complicated detachments. Probing areas of suspicion with the balloon identifies retinal breaks and degrees of traction. When the balloon fails to reattach the retina, information is still provided that helps in planning a minimum procedure for subsequent repair.

Various of the features disclosed herein with respect to specific embodiments may be combined in ways other than those used for representative purposes herein. In order to give some idea of the relative magnitudes of the dimensions here involved, a preferred form of appliance according to this invention has an overall length of about 15 cm, an expandable portion having a maximum diameter of about 8 to 14 mm and a length of about 10 to 15 mm, and a rigid tubular core section through the balloon and adjacent to it of about 3 cm in total length.

I claim:

1. A method of correcting retinal detachments through a small conjunctival incision comprising the steps of inserting an expandable member into Tenon's space to the depth of the break; forming a scleral indentation in the eye by expanding said member; leaving said member in place until subretinal fluid has absorbed and the retina has reattached; and collapsing and removing said member.

2. In a method of correcting retinal detachments including the steps of claim 1, the additional step of leaving said member in place for at least three days after reattachment to promote better adhesion.

3. In a method of correcting retinal detachments including the steps of claim 2, the additional step of collapsing said member in stages prior to removing same.

* * * * *